United States Patent [19]
Kuhn et al.

[11] Patent Number: 5,592,246
[45] Date of Patent: *Jan. 7, 1997

[54] DEVICE AND METHOD FOR MAPPING OBJECTS

[75] Inventors: William P. Kuhn, Tucson, Ariz.; Phillip C. Baker, Orinda, Calif.

[73] Assignee: KeraVision, Inc., Fremont, Calif.

[ * ] Notice: The term of this patent shall not extend beyond the expiration date of Pat. No. 5,475,452.

[21] Appl. No.: 440,512

[22] Filed: May 12, 1995

Related U.S. Application Data

[63] Continuation-in-part of Ser. No. 200,241, Feb. 24, 1994, Pat. No. 5,475,452.

[51] Int. Cl.$^6$ ............................... A61B 3/10; A61B 3/00
[52] U.S. Cl. ..................... 351/212; 351/221; 351/247
[58] Field of Search .................... 351/205, 211, 351/212, 121, 246, 247; 356/138, 139.1, 141.1

[56] References Cited

U.S. PATENT DOCUMENTS

| | | | |
|---|---|---|---|
| 4,440,477 | 4/1984 | Schachar | 351/212 |
| 4,490,022 | 12/1984 | Reynolds | 351/211 |
| 4,685,140 | 8/1987 | Mount, II | 351/212 |
| 4,984,893 | 1/1991 | Lange | 356/376 |
| 5,110,200 | 5/1992 | Snook | 351/212 |
| 5,116,115 | 5/1992 | Lange et al. | 351/212 |
| 5,163,437 | 11/1992 | Fujii et al. | 128/665 |
| 5,357,294 | 10/1994 | Shimizu et al. | 351/212 |
| 5,475,452 | 12/1995 | Kuhn et al. | 351/212 |

OTHER PUBLICATIONS

Aiken, J., et al., "Programmable Liquid-Crystal TV Spatial Light Modulator: Modified Drive Electronics to Improve Device Performance for Spatial-Light-Modulation Operation" *Applied Optics* (1991) 30:4605–4609.

Alexander, B. F., et al., "3-D Shape Measurement by Active Triangulation Using an Array of Coded Light Stripes" *SPIE Optics, Illumination, and Image Sensing for Machine Vision II* (1987) 850:199–209.

Anterior Eye Segment Analysis System EAS–1000 (4 pages total), Nidek Co., Inc., 2460 Embarcadero Way, P.O. Box 50488, Palo Alto, California, 94303.

Arffa, R. C., et al., "Corneal Topography Using Rasterstereography" *Refractive and Corneal Surgery* (1989) 5(6):414–417.

CLASS II Corneal Surface Analyzer Operators Manual (30 pages total), Kera-Metrics Inc., 11211 Sorrento Valley Road, Suite X, San Diego, California 92121.

Cohen, K. L., et al., "Prospective Analysis of Photokeratoscopy for Arcuate Keratotomy to Reduce Postkeratoplasty Astigmatism" *Refractive & Corneal Surgery* (1989) 5(6):388–393.

"Corneal Topography Unit can be Used in OR" *Ocular Surgery News* Oct. 1, 1991, pp. 54, 55.

CorneaScope Photokeratoscope User Manual for Models 900 and 1200 (12 pages total), Kera Corporation, 2362 Walsh Avenue, Santa Clara, California 95051.

(List continued on next page.)

*Primary Examiner*—Huy Mai
*Attorney, Agent, or Firm*—Morrison & Foerster LLP

[57] ABSTRACT

This invention provides a method and apparatus for mapping the surface of an object, in particular, a transparent object such as anterior and posterior surfaces of a patient's cornea, in a clinically useful time using a single optical system. In a preferred embodiment, a pattern generator projects a pattern of light and dark areas onto a patient's cornea, and a light detector receives patterns reflected from the anterior and posterior surfaces of the cornea. A mapping means generates a three-dimensional map of the anterior and posterior corneal surfaces from information regarding the projected and detected light patterns. The invention can be used to map other transparent objects such as a contact lens or an intraocular device, e.g., an intrastromal ring. The invention can also be used to map the surface of an opaque object.

8 Claims, 5 Drawing Sheets

OTHER PUBLICATIONS

Dingeldein, S. A., et al., "Quantitative Descriptors of Corneal Shape Derived from Computer–assisted Analysis of Photokeratographs" *Refractive & Corneal Surgery* (1989) 5(6):372–378.

Dingeldein, S. A., et al., "The Topography of Normal Corneas" *Arch. Opthalmol.* (1989) 107:512–518.

El Hage, S. G. "A Computerized Corneal Topographer for Use in Refractive Surgery" *Refractive & Corneal Surgery* (1989) 5(6):418–423.

Fillard, J. P., "Subpixel Accuracy Location Estimation from Digital Signals" *Optical Engineering* (1992) 31(11):2465–2471.

Frantz, J. M., et al., "A Comparison of Surgical Keratometers" *Refractive & Corneal Surgery* (1989) 5(6):409–413.

Gormley, D. J., et al., "Corneal Modeling" *Cornea* (1988) 7(1):30–35.

Harr, D., "New Sensitivities Enhance Corneal Tomography" *Ocular Surgery News* pp. 10, 18.

Hockwin, O., et al., "Evaluating Cataract Development with the Scheimpflug Camera" pp. 281–318.

"Holography: Closer Look at Tomography" *Ophthalmology Times* Sep. 1, 1991, pp. 1, 50.

Klyce, S. D., et al., "Corneal Topography Comes of Age" *Refractive & Corneal Surgery* (1989) 5(6):359–361.

Klyce, S. D., et al., "Methods of Analysis of Corneal Topography" *Refractive & Corneal Surgery* (1989) 5(6):368–371.

Koch, D. D., et al., "The Corneal EyeSys System: Accuracy Analysis and Reproducibility of First–Generation Prototype" *Refractive & Corneal Surgery* (1989) 5(6):424–429.

Lowans, B. S., et al., "Binary Phase Modulation Properties of a Programmable Liquid–Crystal Television Display" *Applied Optics* (1992) 31(35):7393–7395.

Maguire, L. J., et al., "A Multifocal Lens Effect as a Complication of Radial Keratotomy" *Refractive & Corneal Surgery* (1989) 5(6):394–399.

"Miltiple–Axis Crosshairs" *NASA Tech Briefs* (Feb. 1992) p. 48.

Product brochure for: CLAS 1000 Corneal Laser Analysis System (2 pages), Eye Technology, Inc., 1983 Sloan Place, St. Paul, Minnesota 55117.

Product brochure for: Corneal Modeling System (CMS) (5 pages total), Computed Anatomy, Inc., 28 West 36th Street, New York, New York 10018.

Product brochure for: Corneal Topography Defined, CorneaScope Photokeratoscope (4 pages), Kera Corporation, 2362 Walsh Avenue, Santa Clara, California 95051.

Product brochure for: Corneal Topography System, (2 pages total), Par Technology Corporation, Par Technology Park, 220 Seneca Turnpike, New Hartford, New York 13413.

Product brochure for: EyeSys Corneal Analysis System, (4 pages), EyeSys Laboratories, 2776 Bingle Road, Houston, Texas 77055.

Product brochure for: Kerascan Keratographic Auto Analyzer (6 pages total), Kera Corporation, 2362 Walsh Avenue, Santa Clara, California 95051.

Product brochure for: Visio Computerized Corneal Topographer (2 pages) 5320 Richmond Avenue, Houston, Texas 77056.

Rabinowitz, Y. S., et al., "Computer–Assisted Corneal Topography in Keratoconus" *Refractive & Corneal Surgery* (1989) 5(6):400–408.

"Real–Time Keratometer" *NASA Tech. Briefs* (1988) 12(3):6, 7.

Wang, J., et al., "A New Reconstruction Algorithm for Improvement of Corneal Topographical Analysis" *Refractive & Corneal Surgery* (1989) 5(6):379–387.

Waring, G. O. "Making Sense of Keratospeak II: Proposed Conventional Terminology for Corneal Topography" *Refractive & Corneal Surgery* (1989) 5(6):362–367.

Warnicki, J. W., et al., "Corneal Topography Using Computer Analyzed Rasterstereographic Images" *Applied Optics* (1988) 27(6):1135–1140.

"White–Light, Dispersed–Fringe Interferometric Keratometer" *NASA Tech Briefs* (Feb. 1992) p. 47.

DEVICE AND METHOD FOR MAPPING OBJECTS

CROSS REFERENCE TO RELATED APPLICATION

This application is a continuation-in-part of U.S. patent application Ser. No. 08/200,241, filed Feb. 24, 1994, now U.S. Pat. No. 5,475,452.

BACKGROUND OF THE INVENTION

This invention relates generally to a device and method for mapping a three-dimensional surface and in particular to a device and method for generating and displaying a three-dimensional map of the anterior and posterior surfaces of transparent objects such as a patient's cornea.

Certain ophthalmic surgery procedures require the surgeon to know the shape and thickness of the patient's cornea. For example, when implanting vision correcting devices in a patient's cornea, insertion of the implantable device at the correct location and depth is critical.

The prior art discloses devices for obtaining information about the surfaces of a patient's cornea. Keratometers provide information about the anterior surface of the patient's cornea by projecting rings of light onto the cornea, then measuring the deflection of the light rings by the reflecting corneal surface. Examples of computer-based keratometers may be found in U.S. Pat. No. 4,685,140 and U.S. Pat. No. 5,110,200. One drawback of these devices, however, is that they provide information about the anterior corneal surface only. A second drawback is that these devices rely on specular reflectance of the cornea along an axis perpendicular to the cornea. Placement of the system optics directly in front of the patient's eye could interfere with the performance of surgical procedures on the eye.

Another prior art anterior corneal surface measuring device is shown in Lange U.S. Pat. No. 5,116,115. Lange discloses a system in which a flexible polymer sheet is draped over the anterior corneal surface. Lange projects patterns of lines onto the sheet and uses a camera to receive reflections of the patterns. Measurements of the shifting of the reflected lines is used to generate a map of the anterior corneal surface.

Another type of prior art device is exemplified by the NIDEK EAS-1000 anterior eye segment analysis system. This system uses Scheimpflug photographic techniques to obtain slit images of the patient's eye, i.e., cross-sectional images showing the anterior and posterior corneal surfaces along a single plane through the cornea. While the components of this system may be located away from the axis perpendicular to the eye and will therefore not interfere with any eye surgery, the NIDEK system cannot be used to generate maps of the entire anterior and posterior surfaces of the patient's cornea in a clinically useful time.

Gormley et al. describe a corneal modeling system in "Cornea Modeling," 7 Cornea 30 (1988). The Gormley system uses two separate optical subsystems to obtain information regarding the topography of the anterior corneal surface and the thickness of the cornea, i.e., the distance between the anterior and posterior corneal surfaces. The first optical subsystem is a cylindrical photokeratoscope that projects a 32-ring image onto the anterior surface of the cornea. Reflections of the projected ring pattern are used to generate a topographic image of the anterior corneal surface. The second optical subsystem is a dual-beam scanning laser slit lamp that obtains 14 optical cross-sections of the cornea. The two sets of data points are used to generate a map of the anterior and posterior surfaces of the cornea.

SUMMARY OF THE INVENTION

This invention provides a method and apparatus for mapping the surface of an object, in particular, a transparent object such as anterior and posterior surfaces of a patient's cornea, in a clinically useful time using a single optical system. In a preferred embodiment, a pattern generator projects a pattern of light and dark areas onto a patient's cornea, and a light detector receives patterns reflected from the anterior and posterior surfaces of the cornea. A mapping means generates a three-dimensional map of the anterior and posterior corneal surfaces from information regarding the projected and detected light patterns. The invention can be used to map other transparent objects such as a contact lens or an intraocular device, e.g., an intrastromal ring. The invention can also be used to map the surface of an opaque object.

The invention is described below in further detail with reference to the drawings.

DETAILED DESCRIPTION OF THE PREFERRED EMBODIMENT

The preferred embodiment of this invention uses stereo imaging techniques to measure the surface of the object under test, e.g., the anterior and posterior surfaces of the cornea. A structured pattern of light is projected onto the corneal surface, then imaged onto a detector. By knowing the positions of the elements of the projected pattern and determining their corresponding positions in the detected image, it is possible to construct a three-dimensional image of the anterior surface of the cornea. The same approach can be extended to map the posterior surface of the cornea.

Figure 1:
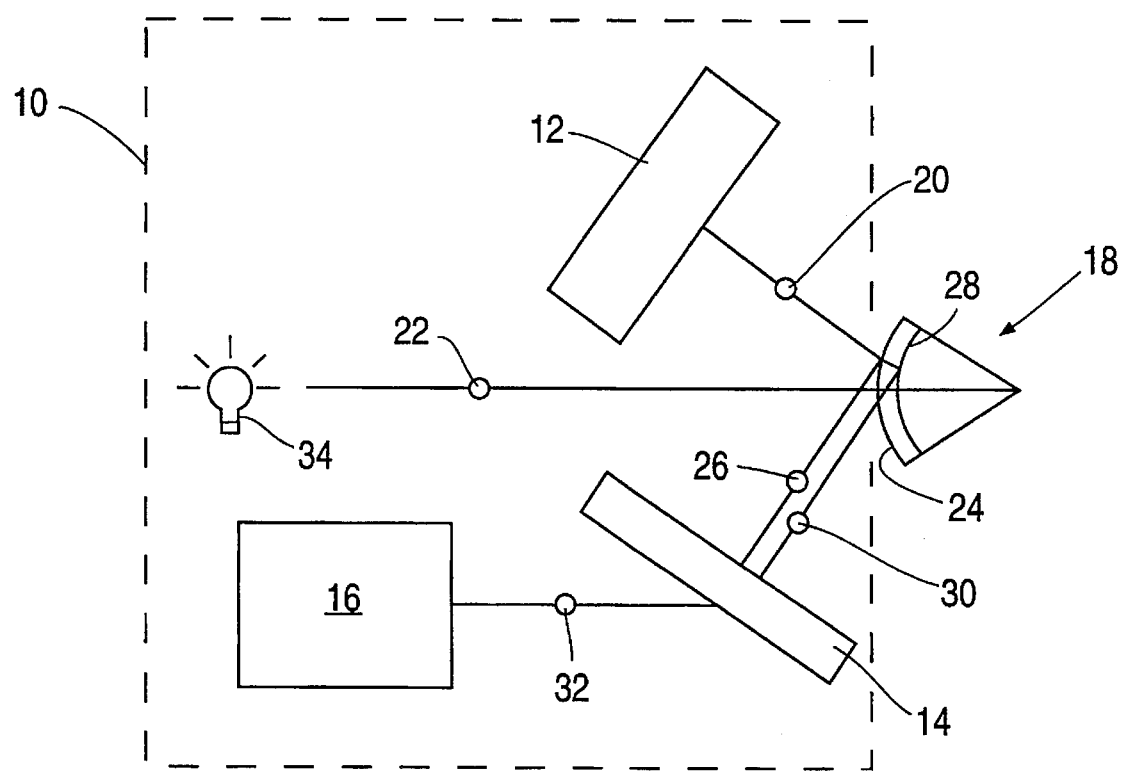
FIG. 1 is a schematic drawing showing the basic elements of the preferred embodiment of this invention.

The principle components of an imaging system 10 according to this invention are shown schematically in FIG. 1: a pattern generator system 12, a detector system 14, and a mapping system 16. The patient's eye is represented schematically by element 18.

Pattern generator system 12 is preferably disposed along an imaginary projection axis 20 disposed at an angle from the normal axis 22 of the patient's eye. In use, pattern generator system 12 projects a predetermined pattern of light and dark areas onto the anterior surface 24 of the patient's cornea. The light generated by pattern generator system 12 may be any frequency of the electromagnetic spectrum for which it is possible to generate and detect. Examples of such frequencies are the visible light spectrum, infrared spectrum, or the like. A single ray of light is shown in FIG. 1 projecting along the projection axis 20. In actual use multiple light areas would be projected in the pattern.

Detector system 14 is disposed along a detection axis 26 at an angle from normal axis 22 that enables the detector system to receive reflections of the projected light pattern from anterior surface 24 as well as reflections from the posterior surface 28 of the cornea. FIG. 1 shows two reflected rays, one along detection axis 26 representing a reflection of the incident ray from anterior surface 24 and another reflected ray 30 representing a reflection of the incident ray from posterior surface 28.

Detector system 14 generates a signal corresponding to each reflected light pattern it receives and sends the signal to mapping system 16 via a suitable signal conductor 32. Mapping system 16 determines the shape of the anterior and posterior surfaces of the cornea from the information contained in the reflected light pattern signals. Mapping system 16 may include a display for displaying a three-dimensional representation of the corneal surfaces.

In order to minimize movement of the patient's eye during the mapping process, the system may include a mechanism for fixing the patient's eye in one place. For example, a dim light source or other object 34 may be placed in front of the patient's eye to provide a fixed point of focus for the patient. Use of this fixation device also sets the visual axis of the patient's eye at a known location for the purpose of building an image of the eye in the manner described below.

Figure 2:
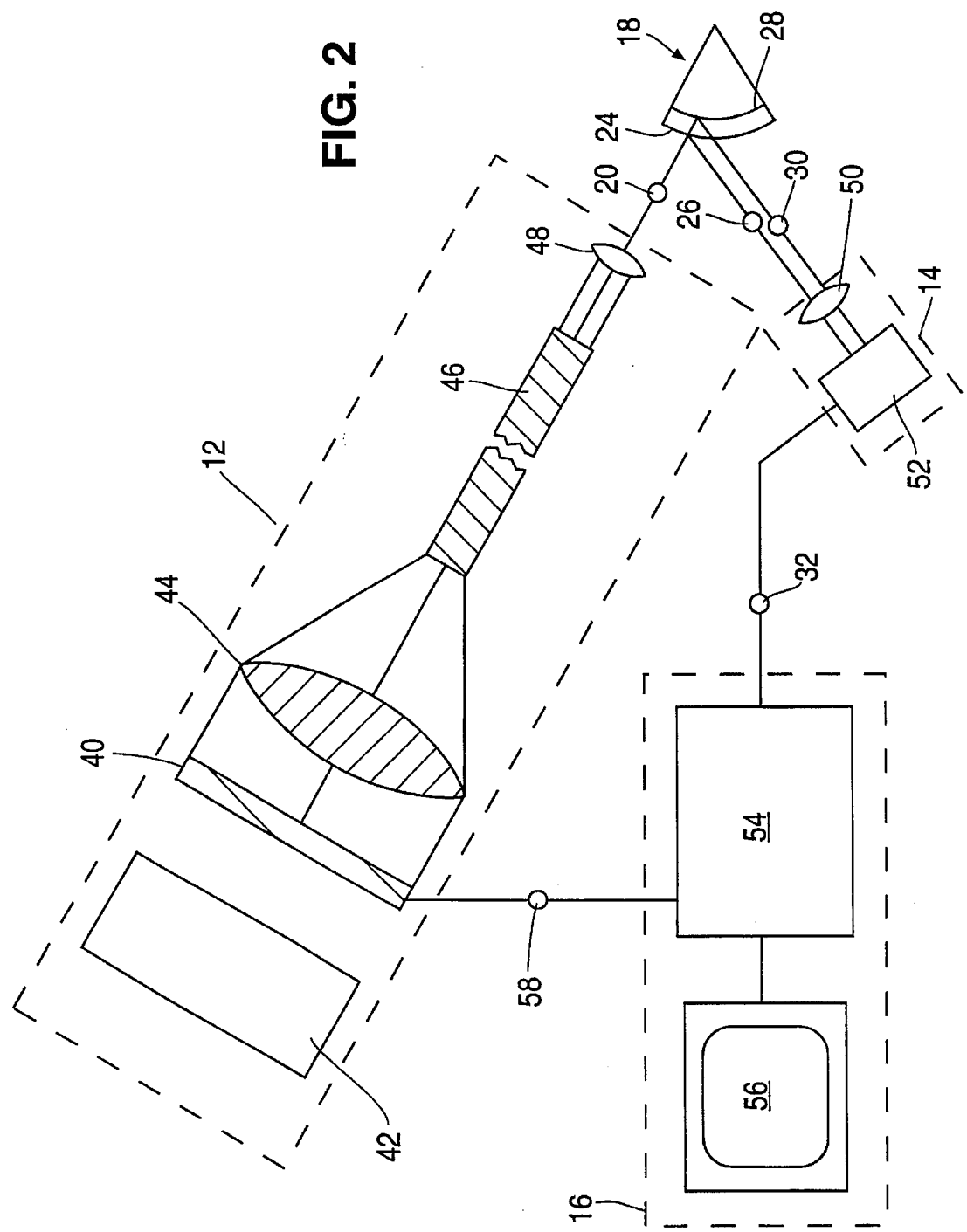
FIG. 2 is a schematic drawing showing preferred embodiments of the pattern generator and mapping means.

FIG. 2 is a schematic representation of a preferred embodiment of this invention showing particular implementations of the pattern generator, detector and mapping systems. In this embodiment, pattern generator system 12 employs an LCD (liquid crystal display) 40 to create patterns of light and dark areas from a light source 42. Light source 42 may be any means known in the art of illuminating an LCD. It will be appreciated that any frequency of the electromagnetic spectrum (such as visible light or infrared or the like) is contemplated by the present invention. In this embodiment, the area of the pattern created by the LCD is larger than the cornea area to be mapped. A relay lens 44 is therefore used to demagnify the pattern. If an alternative pattern generator is used, the relay lens may not be necessary.

It may be desirable to place the light source and LCD at a location remote from the patient. This embodiment therefore provides a light conduit 46, preferably a coherent fiber bundle (also known as an image bundle), to conduct the demagnified light pattern from the LCD to a location near the patient. A projection lens 48 focuses the light pattern from light conduit 48 onto the anterior surface 24 of the patient's eye 18.

Detector system 14 uses a detector lens 50 to receive reflections of the light pattern from the patient's cornea and to focus the reflected light pattern onto a detector 52. In the preferred embodiment, detector 52 is a solid state camera (such as a CCD camera or a CID camera), although another position sensing device known in the art may be used. In order to maximize the operational range of the CCD camera and to prevent saturation of the CCD camera circuitry, the detection axis may be selected to be away from the expected specular reflection axes of the projected light pattern. Thus, the CCD camera would receive only lower-level scattered (diffuse) reflections of the projected light pattern.

Detector 52 generates a signal related to the reflected light pattern it receives and sends that signal to the mapping system 16 via signal conductor 32. While it is not shown in FIG. 2, a second light conduit may be placed between lens 50 and detector 52 to permit the detector to be located at a position remote from the patient.

In the preferred embodiment, mapping system 16 comprises computing means 54 and a display 56. Computing means 54 may be any digital computing system consisting of a central processing unit and digital memory means, such as a personal computer or a specially-designed and dedicated CPU and memory combination, for receiving reflected light pattern information and for generating a three-dimensional map of the reflecting surfaces. Information regarding the three-dimensional shape of the reflecting surfaces 24 and 28 may be displayed on display 56 in contour and isometric maps or in any other manner known in the art.

Figure 5:
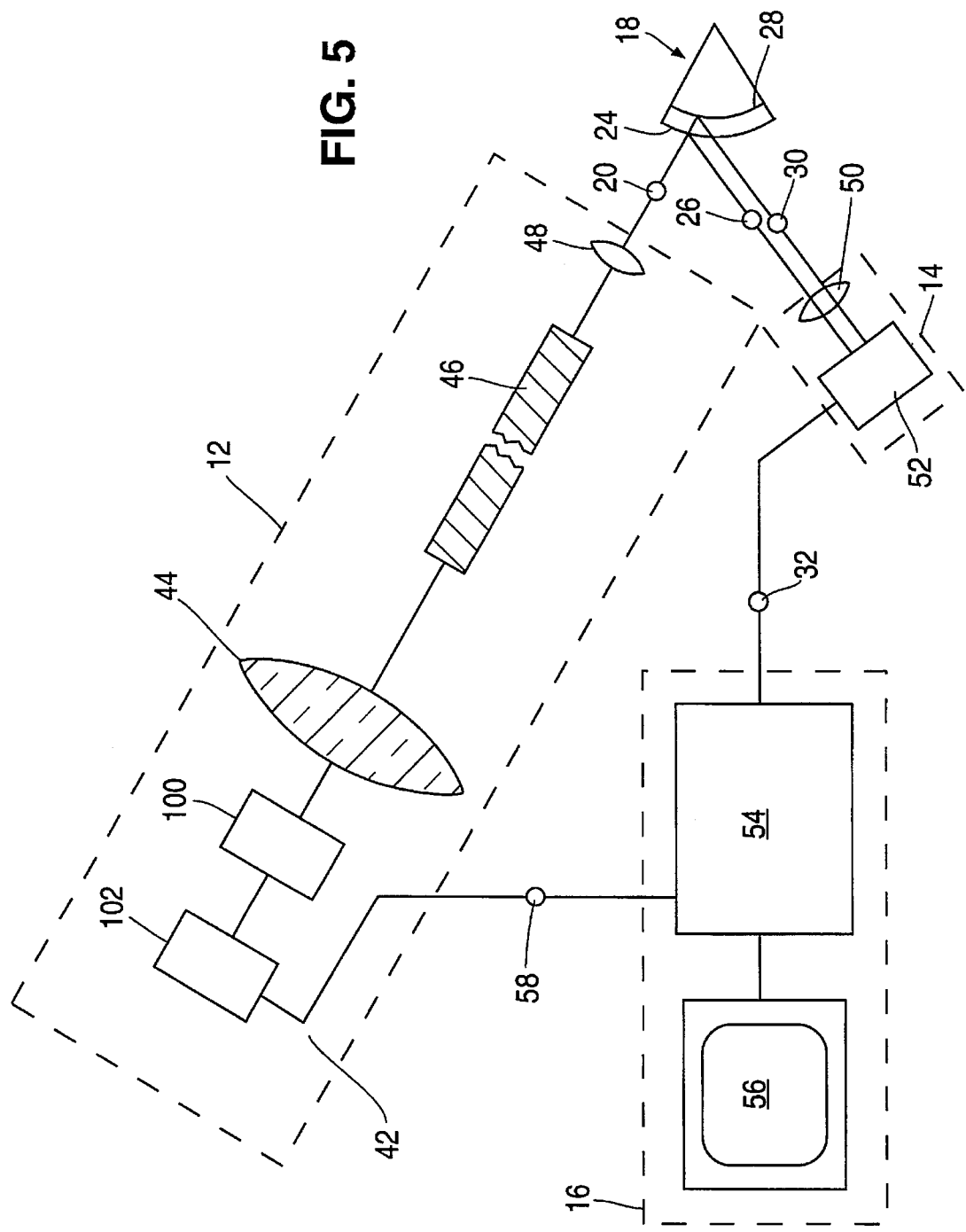
FIG. 5 is a variation of the schematic drawing of FIG. 2 that makes explicit a means for moving a light source.

In the preferred embodiment, computing means 54 controls the operation of LCD 40 via control signals sent on signal conduit 58. Alternatively, the pattern generator may generate light patterns in preset configurations known to computing means 54. In yet another alternative, pattern generator 12 is controlled by an independent controller, and information regarding the projected light patterns is sent to computing means 54 via signal conduit 58. In any event, computing means 54 compares information regarding the projected light pattern with information it receives from the detector system regarding reflected light patterns to map the reflecting surfaces. A preferred method for calculating three-dimensional information to generate the map is described below. FIG. 5 is yet another embodiment showing means for moving a light source 102 coupled to both light source 100 and computing means 54. Means for moving 102 moves light source 100, responsive to signals from computing means 54.

The first step of the mapping method is to align the patient's eye in the region of the intersection of the projection and detection axes. A light pattern is then projected by the pattern generator onto the anterior surface of the patient's cornea. In the preferred embodiment, the light pattern consists of light areas or dots surrounded by dark areas.

Figure 3:
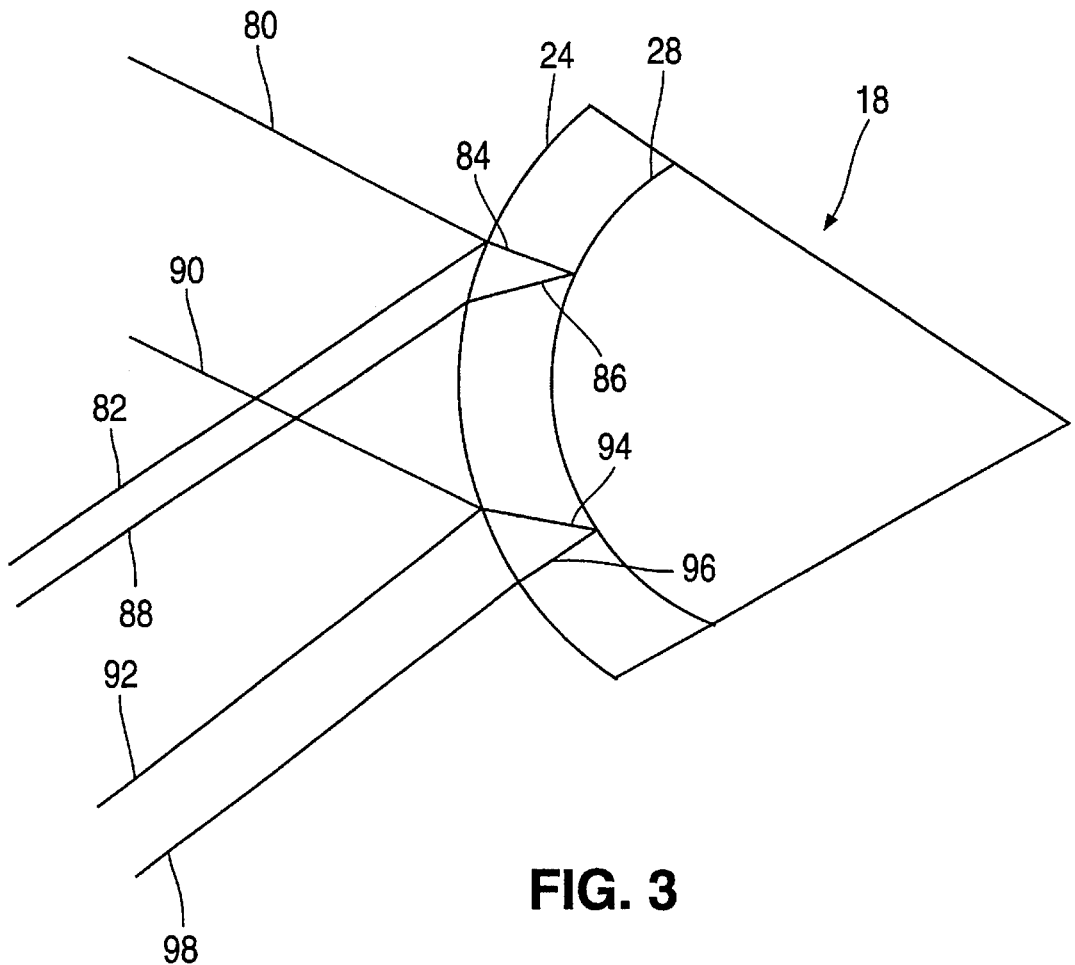
FIG. 3 is a schematic drawing of two projected chief rays and their reflections by the anterior and posterior surfaces of the patient's cornea.

FIG. 3 demonstrates schematically the reflection of two light areas from a projected light pattern by the cornea. The two projected light areas or dots are represented in this schematic drawing by rays 80 and 90. Part of projected ray 80 is reflected by the anterior corneal surface 24 as ray 82, and part passes through the cornea as refracted ray 84. Refracted ray 84 reflects from the posterior surface 28 of the cornea as ray 86, and leaves the cornea as ray 88 after refraction at the anterior surface. The same process occurs for projected ray 90. Thus, the detector receives two reflections of the projected light pattern for each projected light area, one from the anterior surface and one from the posterior surface of the patient's cornea. It should be noted that while FIG. 3 shows the projected and reflected light as one dimensional rays, the projected and reflected light beams actually have cross-sectional areas, as discussed further below.

The detector signal is sent to the computing system which uses a frame grabber to generate a digital representation of the combined anterior and posterior reflected patterns in a manner known in the art. In order to remove the effects of background light, an image corresponding to the absence of a received light pattern is digitized and subtracted from the received light pattern image before further processing is performed. The subtracted information may consist of an average of background lighting levels taken just before and just after the received reflected light pattern.

Figure 4A:
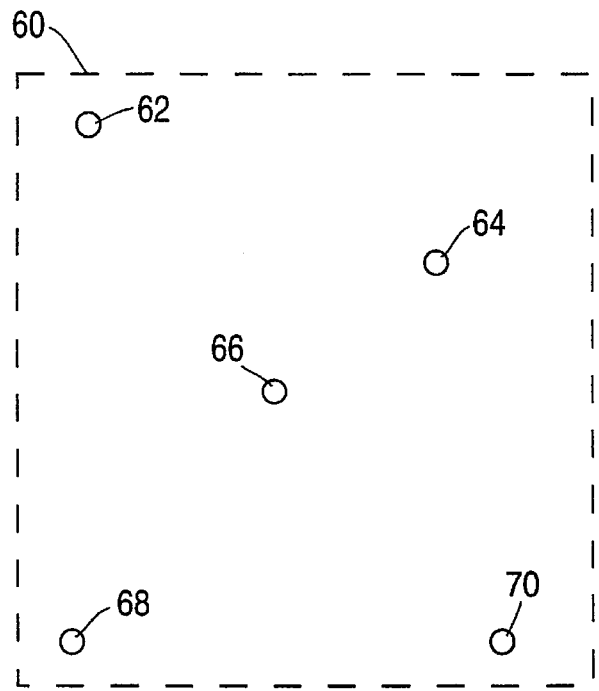
FIG. 4(a) is an example of a projected light pattern according to this invention.
Figure 4B:
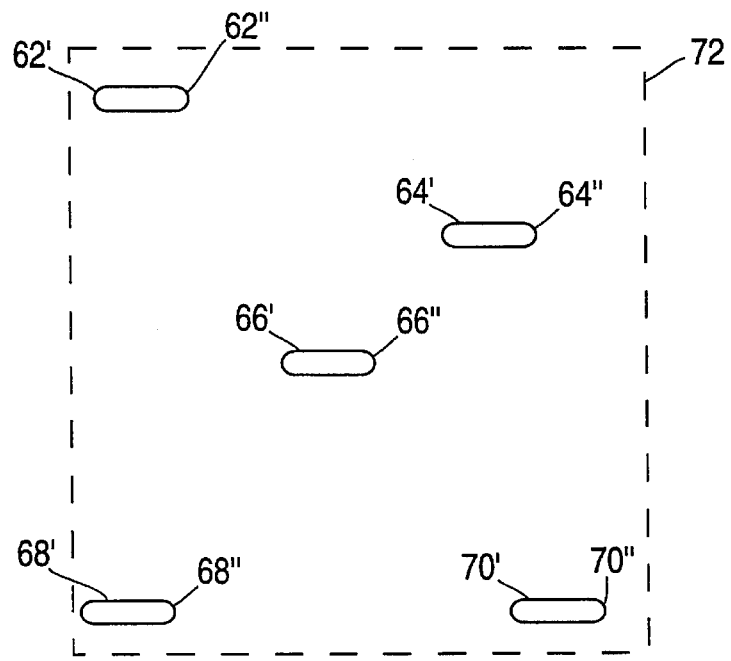
FIG. 4(b) is an example of a reflection of the light pattern of FIG. 4(a) by a patient's cornea.

In the received reflected light pattern, anterior surface reflections are distinguished from posterior surface reflections by comparing the reflected pattern with the projected pattern. An exemplary projected pattern 60 having light areas or dots 62, 64, 66, 68 and 70 is shown in FIG. 4(*a*). A hypothetical received pattern 72 caused by reflection of pattern 60 from a patient's cornea is shown in FIG. 4(*b*).

Received pattern 72 has an elongated light area for each projected dot, which is actually the superimposition of reflections from the anterior and posterior surfaces of the cornea. Thus, as can be seen from FIGS. 4(*a*) and (*b*), one end of each elongated light area corresponds to a reflection from the cornea's anterior surface (ends 62', 64', 66', 68' and 70'), and the other end corresponds to a reflection from the cornea's posterior surface (ends 62", 64", 66", 68" and 70").

The computing system assigns each end of the received elongated area to an anterior surface list or a posterior surface list, depending on the elongated area's spatial relationship to the dots in the projected pattern and the other elongated areas in the received pattern. Also, in addition to their relative positions, the relative intensities of the ends of the elongated areas will be an indication of whether a particular part of the elongated area originated on the anterior or posterior surfaces; reflections from the posterior surface will be weaker.

For every elongated area end in the received pattern, the computing system estimates the chief ray direction, identifies the reflecting surface (i.e., anterior or posterior corneal surface), and associates the detected end with a specific dot in the source pattern. For each elongated area end, the chief ray is the center of the cone of light from the center of the light's source (here, a particular pixel in the generated pattern or in the image reflected from the corneal surface) to the receiving surface (i.e, the corneal surface or the detector). The preferred method of estimating the chief ray direction for each reflected elongated area end received by the detector is to calculate the end's centroid. The direction of the ray from the centroid toward the originating surface (the pattern generator or the cornea) is determined by the optical characteristics of the projection and detector lenses. While imperfect knowledge of the system's optical characteristics may make the estimate imperfect, this estimate nonetheless permits construction of a three-dimensional image of the reflecting surface.

After separating the received pattern areas into anterior and posterior surface lists, the preferred method begins identifying the coordinates of points on the two corneal surfaces by determining the intersections of projected and reflected rays. For example, the computing means calculates the ray directions for rays 80 and 82 of FIG. 3 based on the known initial positions of the dots' centroids in the projected pattern and on the optical characteristics of the projection lens and the angle of the projection axis from the normal axis. Likewise, the computing means determines the ray directions for reflected chief rays 82, 88, 92, and 98 based on the computed centroids of the light dots received by the detector and the known characteristics of the detector lens and the angle of the detection axis from the normal axis. The intersections of the projected and reflected rays can then be calculated and used to map the reflecting surfaces.

It is possible, of course, that the calculated chief rays do not actually intersect due to imperfect knowledge of system parameters or optical aberrations. The preferred method therefore estimates the most likely intersection point by finding the closest point between the two rays. If the distance between the two rays at the closest point exceeds a predetermined maximum, the method rejects this point and does not use it in constructing the surface map.

The corneal surface map may be generated and displayed by commercially available graphics software—such as MatLab by The Math Works, Inc., or Mathematica by Wolfram Research—using the anterior and posterior surface coordinate information determined using the method described above. In addition to this quantitative map, a qualitative gray scale image of the patient's eye may be generated using the same system optics and diffuse light (such as the ambient room light). Because of the off-normal axis orientation of the system optics, the qualitative image will have a distorted perspective that can be corrected in a manner known in the art. The qualitative image may be superimposed on the quantitative image on the system display or the two images may be displayed separately.

While it is possible to generate a map of the anterior and posterior corneal surfaces using a single projected pattern, the preferred method scans sequentially through multiple patterns, projecting each onto the cornea. The coordinate mapping process described above repeats with each projected pattern. In order to gather enough information to build an accurate image of the corneal surfaces, each projected light pattern will need to differ from the others. Maintaining a partial overlap between subsequent projected light patterns, however, will enable the system to determine whether the patient's eye moved between light pattern transmissions and to compensate for the movement. In the preferred embodiment, each light pattern has at least one dot that is in the same location as a dot in the previously projected pattern. The total number of dots in a projected pattern is a matter of design choice. In general, using a greater number of dots in each projected pattern, while keeping the total number of dots per mapping session constant, will reduce data acquisition time but increase the possibility of misassociation of projected and detected dots.

Modifications to the preferred embodiment may be made without departing from the scope of the invention. For example, a spatial light modulator (SLM) may be used in place of the LCD in the pattern generator. In addition, the light source may be white light, color-filtered light, or laser light. Instead of dots, the light patterns can be comprised of stripes or any other suitable shape. For example, a single stripe of light may be scanned across the patient's eye from one side to the other to generate the reflections used to map the corneal surfaces.

In addition, the choice of system components may enable a focusing of the reflected pattern such that the reflected pattern consists of separate dots corresponding to reflections from the anterior and posterior cornea surfaces instead of elongated areas.

As an alternative to a transmissive pattern generator such as an LCD, an array of LED's or other addressable light sources may be used as the pattern generator. Another alternative would be the use of a digital mirror device, such as the one developed by Texas Instruments, to reflect light in specific selectable patterns from a light source.

Instead of scanning the corneal surface by serially projecting different light patterns, the scan may be performed mechanically by moving a single light pattern 100 across the corneal surface by using a mechanical mover 102. The pattern may be a single line or dot. In this alternative embodiment, reflection information would be correlated with information regarding mechanical movement of the light source to determine the spatial coordinates of the reflecting corneal surfaces.

In addition, while the invention has been described with reference to a corneal mapping device and method, the invention may be used to map the three-dimensional surfaces of other transparent objects as well. For example, the device and method described above may be used to map the anterior and posterior surfaces of contact lenses or intraocular devices such as intrastromal rings.

Finally, the invention may be used to map a single surface of a transparent object, such as the anterior surface of a cornea. The invention may also be used to map a surface of an opaque object.

Other modifications will be apparent to those skilled in the art.

All references cited herein are incorporated herein by reference in their entirety.

What is claimed is:

1. A system for mapping the surface of a transparent object, the system comprising:

a light source generating a first pattern of light and dark areas, the light source being positioned to project the pattern onto an anterior surface of the transparent object;

a light detector positioned to receive reflections of the pattern from the anterior surface and from a posterior surface of the transparent object; and mapping means for determining the three-dimensional shape of the anterior and posterior surfaces of the object from the received reflections wherein said light source generates a detectable frequency of electromagnetic radiation.

2. The system as recited in claim 1 wherein said detectable frequency of electromagnetic radiation is infrared radiation.

3. A system for mapping a corneal surface of an eye, the system comprising:

a light source generating first and second patterns of light and dark areas, the light source being positioned to project the patterns serially onto a corneal surface;

a light detector positioned to receive reflections of the first and second patterns from the corneal surface; and mapping means for determining the shape of the corneal surface from the received reflections wherein said light source generates a detectable frequency of electromagnetic radiation.

4. The system as recited in claim 3 wherein said detectable frequency of electromagnetic radiation is infrared radiation.

5. A method for mapping the surface of a transparent object, the method comprising the following steps:

projecting a pattern of light and dark areas along a projection axis onto an anterior surface of a transparent object to create reflected light patterns of light and dark areas from the anterior surface and from a posterior surface along a detection axis;

generating a reflected light pattern signal from the reflected light patterns; and determining the three-dimensional shape of the anterior and posterior surfaces from the reflected light pattern signal wherein said pattern of light and dark areas comprises patterns of detectable electromagnetic radiation.

6. The method as recited in claim 5 wherein said pattern of light and dark areas comprises patterns of infrared radiation.

7. A method for mapping a corneal surface of an eye, the method comprising the following steps:

projecting first and second patterns of light and dark areas serially along a projection axis onto a corneal surface to create first and second reflected light patterns of light and dark areas from the surface along a detection axis;

generating a reflected light pattern signal from the reflected light patterns; and determining the three-dimensional shape of the corneal surface from the reflected light pattern signal wherein said first and second patterns of light and dark areas comprise patterns of detectable electromagnetic radiation.

8. The method as recited in claim 7 wherein said first and second patterns of light and dark areas comprise patterns of infrared radiation.

* * * * *

UNITED STATES PATENT AND TRADEMARK OFFICE
CERTIFICATE OF CORRECTION

PATENT NO. : 5,592,246
DATED : January 7, 1997
INVENTOR(S) : Kuhn et al.

It is certified that error appears in the above-indentified patent and that said Letters Patent is hereby corrected as shown below:

In column 1, line 43, please change "is" to --are--.

In column 5, line 13, please delete ".".

Signed and Sealed this

Eighth Day of April, 1997

Attest:

BRUCE LEHMAN

Attesting Officer     Commissioner of Patents and Trademarks